United States Patent
Manns et al.

(10) Patent No.: US 7,264,928 B2
(45) Date of Patent: Sep. 4, 2007

(54) METHOD FOR THE PREDICTION OF THE RISK POTENTIAL FOR CANCEROUS DISEASES AND INFLAMMATORY INTESTINAL DISEASES AND CORRESPONDING TESTS

(75) Inventors: Michael Manns, Isernhagen (DE); Christian Strassburg, Hannover (DE)

(73) Assignee: Medizinische Hochschule Hannover, Hannover (DE)

( * ) Notice: Subject to any disclaimer, the term of this patent is extended or adjusted under 35 U.S.C. 154(b) by 501 days.

(21) Appl. No.: 10/250,508

(22) PCT Filed: Jan. 3, 2002

(86) PCT No.: PCT/DE02/00003

§ 371 (c)(1),
(2), (4) Date: Dec. 8, 2003

(87) PCT Pub. No.: WO02/053770

PCT Pub. Date: Jul. 11, 2002

(65) Prior Publication Data

US 2004/0121327 A1    Jun. 24, 2004

(30) Foreign Application Priority Data

Jan. 5, 2001    (DE) ................. 101 00 238

(51) Int. Cl.
C12Q 1/68    (2006.01)
C12P 19/34    (2006.01)
C07H 21/02    (2006.01)
C07H 21/04    (2006.01)

(52) U.S. Cl. ................. 435/6; 435/91.2; 536/23.5
(58) Field of Classification Search .............. None
See application file for complete search history.

(56) References Cited

U.S. PATENT DOCUMENTS 5,925,566 A * 7/1999 Davis et al. ............. 435/325

FOREIGN PATENT DOCUMENTS

WO    WO99/57322    11/1999
WO    WO 00/06776    2/2000

OTHER PUBLICATIONS

Vogel, A et al. Genetic link of hepatocellular carcinoma with polymorphisms of the UDP-glucuronosyltransferase UGT1A7 gene. 2001. Gastroenterology. vol. 121 pp. 1136-1144.*
Liu, Vincent et al. Quantitative Allele Specific PCR: Demonstration of Age Association Accumulation in Human Tissues of the A/G Muation at Nucleotide 3243 in Mitochondrial DNA. 1997. Human Mutation vol. 9 pp. 265-271.*
Strassburg, C.P., et al., "Expression of the UDP-glucuronosyltransferase 1A Locus in Human Colon", J.Biol.Chem., vol. 273. No. 15, pp. 8719-8726 (1998).
Strassburg, C.P., et al., "Differential Down-Regulation of the UDP-Glucuronosyltransferase 1A Locus is an Early Event in Human Liver and Biliary Cancer", Cancer Research, pp. 2979-2985 (1997).
Guillemette, C., et al., "Structural heterogeneIty at the UDP-glucuronosyltransferase I locus: functional consequences of three novel missense mutations in the human UGT1A7 gene", Pharmacogenetics, 10:629-644 (2000).
Tukey, R.H., et al., "Human UDP-Glucuronosyltransferases: Metabolism, Expression, and Disease", Ann.Rev.Pharmacol. Toxicol., 40:581-616 (2000).
Vogel, A., et al., "Genetic Link of Hepatocellular Carcinoma With Polymorphisms of the UDP-Glucuronosyltransferase UGT1A7 Gene", Gastroenterology, vol. 121, No. 5, pp. 1136-1144 (2001).
Strassburg, C.P., et al., "Polymorphisms of the human UDP-glucuronosyltransferase (UGT) 1A7 gene in colorectal cancer", GUT, pp. 851-856 (2002).
Strassburg, C.P., et al., Differential Expression of the UGT1A Locus in Human Liver, Biliary, and Gastric Tissue: Identification of UGT1A7 and UGT1A10 Transcripts in Extrahepatic Tissue, Molecular Pharmacology, 52:212-220 (1997).
Hirschhorn, J.N., et al., "SBE-TAGS: An array-based method for efficient single-nucleotide polymorphism genotyping", PNAS, vol. 97, No. 22, pp. 12164-12169 (Oct. 14, 2000).
A. Vogel, et al., Polymorphisms of the Carcinogen Detoxifying UDP-Glucuronosyltransferase UGT1A7 in Proximal Digestive Tract Cancer, Gastroenterol, 40:497-502 (2002).
NCBI Sequence Viewer—U39570 (2pgs).
NCBI Sequence Viewer—U89507 (2pgs).

* cited by examiner

*Primary Examiner*—Diana Johannsen
*Assistant Examiner*—Amanda Shaw
(74) *Attorney, Agent, or Firm*—Whitham Curtis Christofferson & Cook, PC

(57) ABSTRACT

The invention relates to a method for the prediction of the risk potential and/or diagnosis of cancerous diseases or inflammatory intestinal diseases, whereby a DNA sample is tested for the presence of polymorphic UGT1A7 allele. A positive result for a mutation is a positive indication of a sensitivity to cancerous diseases. A prediction of sensitivity to an inflammatory intestinal disease can similarly be made. A PCR amplification of the exon 1, using the DNA sample with subsequent sequence analysis is carried out in the method and the determined sequence compared with that of the wild type and the polymorphic allele. The presence or lack of mutations is monitored by sequencing the corresponding cDNA using automated fluorescent dye sequencing. The test arrangement for requires genetic detection reagents, namely the required primer or cDNAs, on a stationary support in a pre-prepared arrangement or sequence for reading off the results. The recombinant UGT1A7 enzymes are also used for therapeutic purposes.

22 Claims, 3 Drawing Sheets

Figures 1, 2:
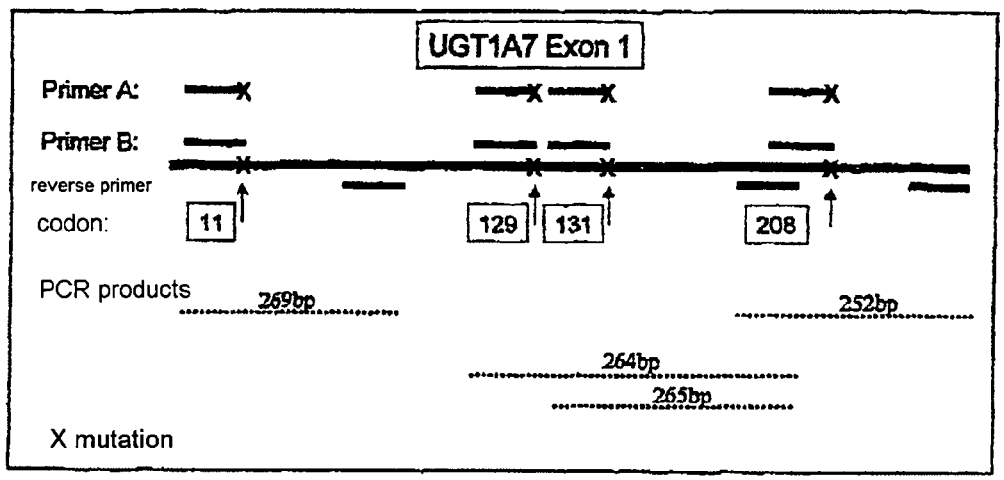

| Allele | | NC | CRC | IBD |
|---|---|---|---|---|
| UGT1A7*1 | wildtype | 48% | 4% | 6% |
| UGT1A7*2 | +/+ | 0% | 0% | 0% |
| UGT1A7*2 | +/- | 5% | 19%* | 3% |
| UGT1A7*3 | +/+ | 16% | 0% | 10% |
| UGT1A7*3 | +/- | 18% | 23% | 10% |
| UGT1A7*4 | +/+ | 7% | 23%* | 26%* |
| UGT1A7*4 | +/- | 3% | 19%* | 16%* |
| UGT1A7*3/ UGT1A7*4 | compound heterozygous | 3% | 12% | 16%* |
| UGT1A7*4 (+/+) and UGT1A7*3/UGT1A7*4 | | 10% | 35%* | 50%* |

| codon no. | 10 11 12 | 128 129 130 131 132 | 207 208 209 | description |
|---|---|---|---|---|
| UGT1A7*1 | CTT CCC CTA <br> L P L | TTT AAT GAC CGA AAA <br> F N D R K | GTA TGG AAC <br> V W N | WT |
| UGT1A7*2 | CTT CCA CTA <br> L P L | TTT AAT GAC CGA AAA <br> F N D R K | GTA CGG AAC <br> V R N | W208R |
| UGT1A7*3 | CTT CCC CTA <br> L P L | TTT AAG GAC AAA AAA <br> F K D K K | GTA TGG AAC <br> V W N | N129K/R131K |
| UGT1A7*4 | CTT CCA CTA <br> L P L | TTT AAG GAC AAA AAA <br> F K D K K | GTA CGG AAC <br> V R N | N129K/R131K/W208R |

Figure 3

| aminoacid no. | aa 7 - 15 | aa 127 - 134 | aa 205 - 213 |
|---|---|---|---|
| UGT1A1 | GGRP-LVLG | LLHNKELM | QRVKNMLIA- |
| UGT1A3 | VPLPWIATG | LLHNEALI | QRVKNMLYP- |
| UGT1A4 | VPLPQIATG | LLHNEALI | QRVKNMLYP- |
| UGT1A5 | VPLPRIATG | LLHNEALI | QRVKNMLYP- |
| UGT1A6 | RSFQRISAG | LLQDRDTL | QRVANFLVN- |
| UGT1A7 | TGLLPLYVC | LFNDRKLV | ERVWNHIMH- |
| UGT1A8 | TSPIPLCVS | LFNDRKLV | ERVRNHIMH- |
| UGT1A9 | TSPLPLCVC | LFKDKKLV | ERVRNHIMH- |
| UGT1A10 | DQPRSFMCV | LFNDRKLV | ERVWNHIVH- |
| UGT1A7 polymorphisms: | | N129K/R131K | W208R |

Figure 4

METHOD FOR THE PREDICTION OF THE RISK POTENTIAL FOR CANCEROUS DISEASES AND INFLAMMATORY INTESTINAL DISEASES AND CORRESPONDING TESTS

RELATED APPLICATIONS

This application is the U.S. National Phase under 35 U.S.C. 371 of International Application PCT/DE02/00003, filed May 8, 2002, which was published in a language other than English and which claims priority of Germany 101 00 238.6, filed Jan. 5, 2001.

The invention relates to a method for predicting the potential risk of carcinomas and inflammatory bowel diseases and for diagnosing these disorders. The invention primarily relates to a method for estimating the potential risk of colorectal carcinomas. The invention further relates to diagnostic tests on DNA samples from an individual to be investigated, and to the use of new polymorphic forms of the UGT1A7 gene for the metabolic characterization of medicaments, especially of tumor therapeutic agents.

The current assumption is that the risk of cancer is determined by a genetic predisposition and by environmental effects including exposure to carcinogenic substances.

It has therefore frequently been assumed that there is an association between genetic polymorphisms of carcinogen-metabolizing enzymes and the development of a cancer. However, specific, statistically confirmed associations are difficult to find because the metabolizing cannot be equated with a detoxification. For predicting the risk of cancer it is therefore insufficient just to detect genetic modifications; on the contrary, it is necessary to know that the change leads to clearly adverse metabolic consequences.

A further problem in finding such an association is that the human metabolism is very complex and an enormous number of substances, including metabolites, proteins and in particular also enzymes, might be suitable markers for a risk of cancer. This also applies to colonic or colorectal carcinoma (CRC), one of the commonest types of cancer in the western world. The human intestine is a large organ influenced by many types of body processes and also the diet. It was therefore necessarily doubtful whether an unambiguous estimation of the risk on the basis of a genetic predisposition is in fact possible.

A large number of enzyme classes are involved in intestinal metabolism, including those responsible for metabolizing foreign substances.

Human uridine diphosphate (UDP) 5'-glucuronosyltransferase (UGT) is a large class of enzymes bringing about the glucuronidation of numerous substrates. Within this super family, three families with particular tasks have been identified, UGT1, UGT2 and UGT8. Numerous isoforms are distinguished among the enzymes of the UGT1 family alone. In the last 10 years, 5 UGT isoforms of the 1A family (UGT1A1, 1A3, 1A4, 1A6 and 1A9) have been discovered in the liver and cloned, including the bilirubin UGT isoform UGT1A1. Three extrahepatic UGT1A gene products have been isolated from the biliary tract (UGT1A10), stomach (UGT1A7) and colon (UGT1A8).

The proteins encoded on the human UGT1A7 gene locus serve, through the glucuronidation, the detoxification of a large number of endogenous and exogenous (xenobiotic, i.e. compounds of industrial origin which are difficult to degrade) compounds in the human body. They are proteins of the so-called phase 2 metabolism in humans, which includes for example acetylation, sulfation and glucuronidation. UGT1A7, which was described as transcript for the first time in 1996, has been demonstrated to detoxify polycyclic hydrocarbons and heterocyclic amines. These substances are also regarded as carcinogens.

WO 00/06776 discloses the identification of genetic polymorphisms in human UGT2B4, UGT2B7 and UGT2B15 genes which modify UGT2B activity. UGT2 enzymes are involved inter alia in steroid metabolism. Nucleic acids which contain the polymorphic UGT2 sequences have been used to screen patients for an altered metabolism of UGT2B substrates, possible drug-drug interactions and adverse effects/side effects, and for diseases derived from exposure to environmental or occupational poisons. Animal, cell and in vitro models of drug metabolisms has [sic] been established with the aid of the nucleic acids.

Genetic polymorphisms in the human UGT1 gene which modify the UGT1-dependent drug metabolism were identified in WO 99/57322. Once again, the polymorphic sequences were used to screen patients for an altered metabolism of UGT1 substrates, possible drug-drug interactions and adverse effects/side effects, and for diseases derived from exposure to environmental or occupational poisons. In turn, animal, cell and in vitro models of drug metabolisms were established with the aid of the nucleic acids.

In addition, functional consequences of a genetic modification of the human UGT1A7 gene have already been described in "C. Guillemette, J. K. Ritter, D. J. Auyeung, F. K. Kessler, D. E. Housman; "Struktural [sic] hetreogeneity [sic] at the UDP glucuronosyltransferase 1 locus: functional consequences of three novel missense mutations in the human UGT1A7 gene", Pharmacogenetics, 2000, 10: 629-644". It is also suggested therein that UGT1A7 has a possible role in the detoxification and elimination of carcinogenic products in the lung. UGT1A7 is expressed in the lung but not in the human large bowel.

The object of the invention was to find a specific association between a risk of cancer, especially of colonic carcinoma (colorectal carcinoma CRC) and genetic dispositions and to provide a test for detecting this disposition.

This has been achieved by finding new polymorphic UGT1A7 alleles which have been named UGT1A7*2, UGT1A7*3 and UGT1A7*4 and for which it is possible to show with statistically astonishing relevance an association with the occurrence of a colorectal carcinoma (CRC) and moreover with particular inflammatory bowel disorders (IBD; Crohn's disease) and with the types of cancer pancreatic, hepatic, gastric and esophageal cancer. This result is surprising inasmuch as UGT1A7 is not expressed in the large bowel, i.e. not in the diseased region. It is astonishing and has not been found in previous investigations that a genetic predisposition does not depend on expression in the relevant organ but is also possible in a spatially separate manner. It is evident from this that the genetic modification must have a global and not just an organ-specific effect. It has been possible to show such an association here for the first time.

The genetic polymorphisms are those of the germ line and not somatic mutations of the tumor. The underlying analyses were carried out on genomic DNA from lymphocytes of patients with tumors (CRC), inflammatory bowel disease (IBD) and reference subjects not having these disorders. The result of analysis of a total of 111 individuals is that the polymorphisms in the individual codons do not occur independently of one another but can be inherited only in combination.

UGT1A7*2 is characterized by a silent mutation at codon 11 with a change from C to A at position 3 (CCC to CCA). This mutation is located in the signal peptide domain of the endoplasmic reticulum. This is associated with a second mutation at codon 208, specifically W208R, a change from T to C, which leads to a non-conservative replacement of an aromatic tryptophan by a positively charged arginine residue. The polymorphism at codon 208 is located in a sequence region which is conserved not just in the first exons of UGT1A7-10 but in all members of the UGT1A7 family. The presence of an RV-N sequence motif between amino acids 206 and 209 is common to all UGT1A proteins. The W208R exchange in UGT1A7 represents the wild-type sequence of UGT1A8 and UGT1A9. The applicant's investigations show that the polymorphisms at codon 11 and at codon 208 do not occur singly (in a study on 111 people). Characterization of individuals heterozygous at both positions, and the fact that it was not possible to find any individually homozygous pattern at codon 11 or at codon 208, suggests that both exchanges are located on the UGT1A7*2 allele.

UGT1A7*3 comprises two mutations. The first is a T to G change at codon 129, resulting in a conservative codon exchange from asparagine to lysine (N129K). The second is evident at codon 131 in a double change from C to A at position 1 and G to A at position 2 of the codon, leading to an arginine to lysine exchange (R131K). This polymorphism likewise affects highly conserved sequences of the UGT protein. The leucine-127 which is present in all UGT1A7 proteins is followed by an LHN-L motif (amino acids 128-133) which is conserved in UGT1A1, UGT1A3, UGT1A4 and UGT1A5. An F-D-KLV amino acid motif is conserved at amino acid position 128-134 in UGT1A7, UGT1A8, UGT1A9 and UGT1A10. Analysis of the N129K and R131K polymorphisms showed that these exchanges do not occur independently of one another. Homozygous UGT1A7*3 alleles were identifiable, showing that the N129K/R131K mutations can be identified on a single allele which occurs independently of UGT1A7*2. The N129/R131K polymorphism of UGT1A7 corresponds to the wild-type sequence of UGT1A9 at these codons, further suggesting that the 3 base pair mutations are inherited as a haplotype.

The third allele, UGT1A7*4, combines all the changes observed in UGT1A7*2 and UGT1A7*3. Individuals with homozygous mutations at codons 11, 129, 131 and 208 have been found, indicating that all 4 polymorphisms may occur on a single allele. It is noteworthy that there was single heterozygous or homozygous occurrence of the polymorphisms at codons 11, 129, 131 or 208. This observation also supports, as indicated above, the assumption that the polymorphisms at codons 11 and 208 and likewise at codon 129 with codon 131 are inherited as haplotypes.

On the basis of these results, the object is achieved according to the invention by a method for predicting the potential risk of carcinomas or inflammatory bowel diseases and/or for diagnosing carcinomas or inflammatory bowel diseases, in which a DNA sample from a person to be investigated is tested for the presence of polymorphic UGT1A/alleles which include mutations at codons 11, 129, 131 and/or 208.

In particular, moreover, a positive result from a mutation at codon 11 and codon 208 is regarded as a positive sign of sensitivity for carcinomas, specifically for colorectal carcinoma or colonic carcinoma (CRC). Possible tests therefor are indicated below. A further development of the invention provides an additional check that the mutations regarded as positive are a W208R exchange and a silent mutation of codon 11 from CCC to CCA.

A positive result for mutation at all four codons 11, 129/131 and 208 is moreover regarded according to this invention as an indicator of a sensitivity for an inflammatory bowel disease, in particular the diseases comprised by the term inflammatory bowel disease (IBD) and ulcerative colitis, and a carcinoma, specifically CRC. A check that the mutations regarded as positive are N129K, R131K and W208R, and the silent mutation of CCC to CCA at codon 11, can be provided in relevant tests.

The identified association of UGT1A7 polymorphisms and colorectal carcinoma and inflammatory bowel diseases, which in turn form a risk factor for colon carcinogenesis, make [sic] it possible to use the markers described herein for identifying patients at risk of tumors. Since the detoxification enzymes for which polymorphisms were detected here carry out a global function in the human body, it is probable that relevance goes beyond the colorectal carcinoma described herein to include other cancers of the gastrointestinal tract, of the respiratory system, of blood formation and of the sex organs and glands.

One advantage of the invention is that patients can be assigned at an early date to appropriate risk groups and referred for preventive treatment, leading to an improvement in early detection.

A further advantage of the invention is that the method can also be used for diagnosis. One improvement in diagnosis is a possibility of obtaining even more quickly a clear result on the condition of the patient and accordingly of giving treatment earlier and in a more targeted manner. Early detection and immediate therapy are of crucial importance in particular for carcinomas. CRC can if detected early be prevented or cured in most cases.

Genomic DNA from lymphocytes is preferably used for an investigation. The genomic DNA can be isolated from a sample of the subject's blood by methods of column chromatography and chemical processing. This genomic DNA, which represents the genotype of the person to be investigated, forms the basis for all further genetic test strategies.

There is firstly a general provision for the DNA obtained from the patient to be amplified by the polymerase chain reaction.

A possibility for this in a first embodiment of the invention is to carry out a PCR amplification of the complete exon 1 of the UGT1A7 gene (about 855 base pairs), followed by a sequence analysis. The sequence found can be analyzed in a suitable way, i.e. be compared with the sequence of the wild type and of the UGT1A7 alleles UGT1A7*2, UGT1A7*3 and UGT1A7*4 which are relevant to this method.

In another embodiment, the only cDNA fragments to be amplified are those intended to provide information about the mutations which are sought. The DNA sample is therefore preferably treated with specific primer pairs, of which in each case one binds upstream and one binds downstream of the relevant mutated DNA regions around codons 11, 129/131 or 208, and cDNA fragments which match corresponding fragments of the wild-type allele or of the polymorphic alleles are generated in a polymerase chain reaction, and the presence of mutations at codons 11, 129, 131 and/or 208 is subsequently detected with the aid of sequencing and/or hybridization techniques.

The primer pairs used are preferably those which bind in each case approximately 50 base pairs upstream and downstream of codon 11, of codon 129/131 and of codon 208, resulting in cDNA fragments about 100 to 150 base pairs in size.

Detection of the polymorphisms with sequencing and/or hybridization methods can take place in various ways. The skilled worker is in principle free to select suitable methods from those known to him.

The polymorphisms which are sought can be investigated inter alia by single strand conformation polymorphism analysis (SSCP) by detecting the complete recombination of a patient's cDNA fragment obtained by the preceding PCR with a cDNA fragment, corresponding in each case, of the wild-type allele to give double strands. The underlying principle is based on the fact that an altered DNA sequence is unable to form completely congruent double strands with the wild-type sequence. This can be revealed by gel electrophoresis for the screening investigation and indicates the existence of a mutation. In a modification of this method, the polymorphic cDNA fragments can be detected by temperature gradient gel electrophoresis (TGGE).

The presence or absence of mutations would preferably be checked by sequencing the relevant cDNA by means of automated fluorescent dye sequencing.

A further possibility for detection is to reveal the presence of a polymorphism in a purely PCR-based strategy (amplification refractory mutation system) through specific primer sequences which bind at their 3' terminus to the base exchange of the polymorphism. At the same time, this method can be modified to discriminate between heterozygous and homozygous carriers. One exemplary embodiment of this method is indicated as automatable test kit system as example hereinafter. The primers used are oligonucleotides which bind on the one hand the wild-type sequence and on the other hand the polymorphic sequence, and corresponding reverse primers (antisense primers). Using these, a PCR product is always obtained only if the wild type encoded on the primer or the primer-encoded polymorphic allele is present. The controls employed are defined cDNAs comprising defined polymorphisms. The method can be automated for example by using the quantitative Taqman PCR.

The PCR conjugates can be detected in a conventional way using fluorescent dyes or enzyme markers. Sufficiently suitable techniques are available for the skilled worker to select for this purpose, and there is no need to give a special description thereof here.

The invention also encompasses test kits or test arrangements for carrying out the method of the invention.

The test arrangement belonging to this invention comprises in principle at least the genetic detection reagents necessary for the method, namely the necessary primers or cDNAs, on a stationary support in an arrangement or sequence prepared for reading the result, there being provision for the prepared and additionally labeled DNA samples of the individual for investigation to be brought into contact with the test arrangement, to bind to one of the detection reagents and to be detected with the aid of the marker at this site. It is possible in this connection for the subject's DNA to be labeled with fluorescent dyes or radioactive isotopes.

For a combined analysis of a plurality of UGT1A7 polymorphisms, which is expedient in every case, the various detection reagents necessary for this purpose, i.e. for example the primers for the various codons 11, 129/131 and 208 or the DNA fragments of wild-type and UGT1A7*2/3/4 alleles can, depending on the chosen strategy, be immobilized together on a test arrangement, e.g. on a gene chip.

In order to facilitate reading of the results, it is advantageous for an inscription or an imprint assigned to the detection reagents to be arranged on the stationary support.

Combined analysis of all UGT1A7 polymorphisms is possible by a gene chip technique. For example, the oligonucleotide sequence of the polymorphisms and of the wild type can be immobilized in the stationary phase. Corresponding oligonucleotides from the subject's DNA are amplified by PCR and labeled by fluorescent dyes, radioactive isotopes or other conjugates. The subsequent hybridization reaction identifies the corresponding oligonucleotide on the gene array and determines the existence of a polymorphism. Various embodiments of an array-based test strategy are possible and can be adapted to this method by the skilled worker.

According to a further aspect of the invention, the polymorphic UGT1A7*2, UGT1A7*3 and UGT1A7*4 genes can be used to prepare relevant UGT isotypes. The identified polymorphisms can be expressed as recombinant proteins and be employed for example for metabolic characterization of tumor therapeutic agents in order to make a prediction of the metabolism of these substances possible. Likewise, all polymorphisms of UGT1A7 can be used to investigate the metabolism of potentially mutagenic or carcinogenic substances with the aim of making predictions about their toxicity or carcinogenic potency. For this purpose, the polymorphic alleles are expressed in heterologous expression systems, in bacteria, eukaryotic cell cultures and used subsequently as enzyme preparation for catalytic analyses. Test kits comprising a series of different polymorphism proteins makes simple in vitro analysis possible in this case.

The identification of susceptibility markers for colonic carcinoma and inflammatory bowel diseases makes it possible in principle to use them for gene therapy strategies. Possible uses in gene therapy in principle are currently known to the skilled worker, so that various implementation possibilities are open. The use of UGT1A7 alone or in combination with other homologous members of this enzyme family in tumor therapy is an application of the defined genetic association.

The invention therefore also encompasses the use of UGT1A7 genes or gene fragments for preparing a medicament for gene therapy treatment in the case of UGT1A7 polymorphisms of the UGT1A7*2, UGT1A7*3 and UGT1A7*4 type.

In a further development of the invention, therefore, the oral or parenteral use of the recombinant protein of genes of the UGT1A family in tumor therapy or in tumor prevention in patients at risk is provided. The vectors which can be used for transporting UGT1A7 cDNA or homologous UDT1A cDNAs into human cells and tumor cells are those known in principle to the skilled worker and selectable by him using his expert knowledge. This leads to expression of the protein in the target tissue including embryonic or fetal tissue, where the UGT1A7 medicament for gene therapy can be used to modify precursor cells.

The UGT1A cDNA can be transported for example by parenteral vectors having organ-specific promoters, by intramuscular injection of UGT1A cDNA or by liposome-packaged cDNA through the gastrointestinal tract. The skilled worker is able to pick out suitable delivery systems with the aid of his expert knowledge.

The invention is explained in more detail below by means of examples and figures.

EXAMPLE 1

Test Example

Oligonucleotides (primers) which bind on the one hand the wild-type sequence and on the other hand the polymorphic sequences, and corresponding reverse primers (antisense primers) are used. A PCR product results with them only if the wild type encoded on the primer or the primer-encoded polymorphic allele is present. The principle is depicted in FIG. 1. Defined cDNAs comprising the defined polymorphisms are employed as controls.

The primers used are depicted in table 1:

TABLE 1

| Polymorphism | Type of primer | Sequence | Product size |
|---|---|---|---|
| Codon 11 | A | gggtggactggcctccttcca | 269 bp |
|  | B | gggtggactggcctccttccc |  |
|  | reverse | ggcaaaaaccatgaactcccg |  |
| Codon 129 | A | tttttttcaaattgcaggagtttgtttaag | 264 bp |
|  | B | tttttttcaaattgcaggagtttgtttaat |  |
| Codon 131 | A | aaattgcaggagtttgtttaaggacaa | 271 bp |
|  | B | aaattgcaggagtttgtttaatgaccg |  |
|  | reverse | ttctaagacattttttgaaaaaatagg |  |
| Codon 208 | A | gacgccatgactttcaaggagagagtac | 252 bp |
|  | B | gacgccatgactttcaaggagagagtat |  |
|  | reverse | tggctttccctgatgacagttgatacc |  |

On use of these primers in automated quantitative PCR, conjugates with fluorescent dyes, enzymatic markers or other labeling systems for DNA are prepared and used for this diagnosis. The labeling agents are generally known and are not specially described here.

Results specifically detecting the presence of homozygous and heterozygous mutations are found with the aid of this test system. The results are depicted in table 2.

Test Series on 111 Subjects

The samples were collected from 111 patients of the Department of Gastroenterology and Hepatology of Hannover Medical School in 1999.

The following groups were investigated:
a) the control group (n=54, 44.32±15.65 years, 31 male/23 female) was defined as patients who had no finding of previous cancers, precluded by abdominal ultrasound and endoscopy (upper and lower).
b) colorectal cancer patients (n=26, 62.15±11.25 years, 15 male/11 female) suffered from colorectal carcinoma, as confirmed by exclusion according to the Amsterdam II criteria.
c) the examples of inflammatory bowel diseases (IBD) (n=31, 36.74±11.79 years, 14 male/16 female) comprised patients with ulcerative colitis (n=14, 35.07±13.86 years, 9 male/5 female) and Crohn's disease (n=17, 38.12±10.00 years 5 male/12 female). The diagnoses of ulcerative colitis and of Crohn's disease were based on findings of upper and lower endoscopy and were confirmed by histology of intestinal biopsies.

Genomic DNA: The gemonic DNA was prepared from whole blood samples using the QuiaAmp® system in accordance with the manufacturer's recommendations (Quiagen, Hilden, Germany). Concentration data were determined by spectrophotometry at 260 and 280 nm, and the samples were stored in 10 mM Tris/EDTA buffer (pH 8.0) at 4° C. until investigated further.

Analysis of the UGT1A7 exon 1 sequence: The UGT1A7 exon 1 sequence was amplified by the polymerase chain reaction. The forward primer was from base pair 61 to 38 upstream of the ATG start codon (GenBank access number U39570) of UGT1A7 (5'-gcggctcgagccacttactatattatag-gagct-3'). The reverse primer was between base pair 855 and 829 (GenBank access number U89507) of the UGT1A7

TABLE 2

| | | Controls | | | | Results | | |
|---|---|---|---|---|---|---|---|---|
| Codon | Primer | UGT1A7*1 | UGT1A7*4 | UGT1A7*2 | UGT1A7*3 | UGT1A7*2/ UGT1A7*1 | UGT1A7*2/ UGT1A7*3 | UGT1A7*3/ UGT1A7*4 |
| 11 | A | − | + | + | − | + | + | + |
|  | B | + | − | − | + | + | + | + |
| 129 | A | − | + | − | + | − | + | + |
|  | B | + | − | + | − | + | + | − |
| 131 | A | − | + | − | + | − | + | + |
|  | B | + | − | + | − | + | + | − |
| 208 | A | − | + | + | − | + | + | + |
|  | B | + | − | − | + | + | + | + |

The use of these analyses for all three polymorphic gene loci 11, 129/131 and 208 is therefore of great importance because the presence of the UGT1A7*2 allele (codon 11 and 208) and of the UGT1A7*4 allele (codon 11, 129, 131, 208) are [sic] associated with colorectal carcinoma, but only the presence of the UGT1A7*4 allele are [sic] associated with inflammatory bowel diseases. The genetic analysis therefore expediently consists of combination of the analyses at the identified loci in the sense of a test kit.

exon 1 sequence (5'-gcggatatccataggcactggctttccctgatgaca-3'). Location of the upstream primer outside the open reading frame was necessary in order to achieve specificity of amplification, because the exon 1 sequence of UGT1A7-10 has homologies of 93%. A product 916 base pairs in size was amplified in a volume of 100 μl comprising 10 mM KCl, 20 mM Tris-HCl (pH 8.8), 10 mM ammonium sulfate, 2 mM magnesium sulfate, 1% Triton X-100, 0.2 mM each dNTP, 20 ng of genomic DNA, 2 μM primer and 5 units of VENT (exo) DNA polymerase (NEB, Beverly, Mass.). After a hot start at 94° C. for 3 minutes, 30 cycles of 94° C. for 3 seconds, 57° C. for 30 seconds and 72° C. for 30 seconds were run on a Perkin Elmer Gene Amp PCR 2400 system. The products were visualized in a 2% agarose gel electrophoresis and purified using QuiaQuick® columns according to the manufacturer's statements (Quiagen, Hilden, Germany). The sequences of the PCR products were determined on both strands by automated fluorescent dye sequencing (MWG-Biotech, Ebersbach, Germany). The sequence data were analyzed using the PC gene software package (Oxford Molecular, Campbell, Calif., USA). The statistical analysis was calculated using the Kruskal-Wallis test.

GenBank accession numbers: UGT1A7*1: U89507; UGT1A7*2: AF2969226; UGT1A7*3: AF292627, UGT1A7*4 AF292627

Figure 5:
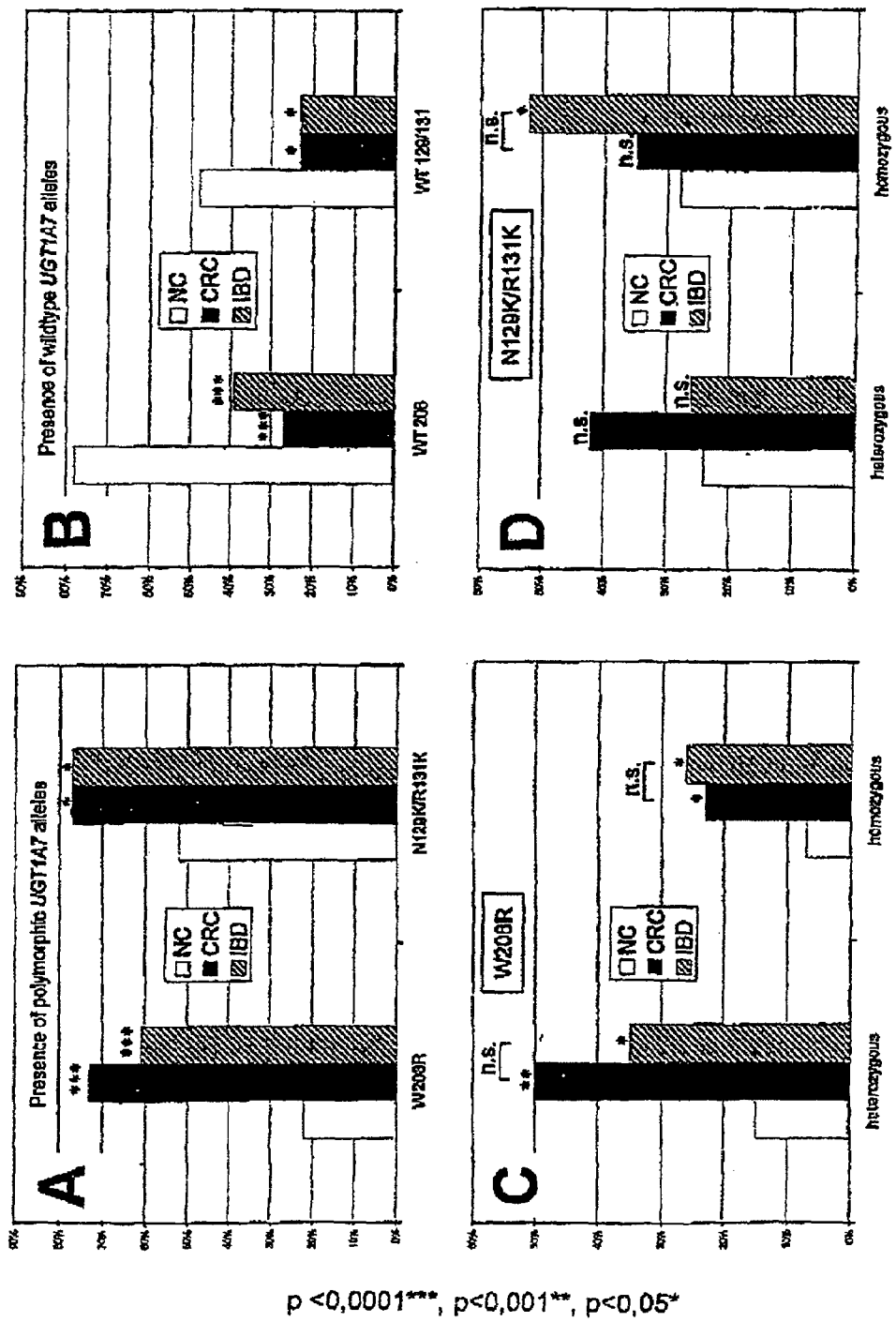

The invention is explained in more detail by means of figures below, these specifically showing:

FIG. 1 graphical representation of the UGT1A7 polymorphism diagnostic method;

FIG. 2 association of UGT1A7*2 and UGT1A7*4 with NC, CRC and IBD;

FIG. 3 3 polymorphic sites of the human UGT1A7 exon 1 sequence;

FIG. 4 comparison of the regions around codon 11, 129, 131 and 208;

FIG. 5 associations between the W208R mutation and colorectal carcinoma and inflammatory bowel diseases.

FIG. 1 shows a UGT1A7 polymorphism diagnostic method in which the region around the identified polymorphisms is amplified by polymerase chain reaction (PCR). Specific primer pairs which bind about 50 base pairs upstream and downstream of codon 11, of codon 129/131 and of codon 208 are used for this. This PCR generates complementary deoxyribonucleic acid fragments (cDNAs) which are 100 to 150 bp in size and which correspond to the wild-type allele or carry the identified polymorphisms.

FIG. 2 shows the analysis of the prevalence of the polymorphic UGT1A7 alleles as defined in FIG. 3. This analysis, which is based on the defined polymorphic UGT1A7 alleles, shows a significant association of UGT1A7*4 and UGT1A7*2 with colorectal cancer (CRC) and the low occurrence of these alleles in the normal control group (NC). In contrast thereto, inflammatory bowel diseases (IBD) are associated only with the presence of UGT1A7*4. No significant association with the UGT1A7*3 allele was found either for CRC or for IBD. The association of linkages of the heterozygous UGT1A7*3/UGT1A7*4 individuals with CRC and IBD was, however, significant. Statistically significant comparisons are indicated by *. UGT1A7*2 is defined as a combination of CCA at codon 11 and the W208R mutation. This is based on the observation that the two mutations are always identified in combination and not individually heterozygous or homozygous either at codon 11 or codon 208. UGT1A7*2 was not detected as homozygous allele. UGT1A7*3 is defined only by the combination of N129K and R131K. These patents [sic] were either homozygous or heterozygous both for N129K and R131K. The heterozygous UGT1A7*4 may alternatively represent the linkage heterozygous UGT1A7*2/ UGT1A7*3.

FIG. 3 shows a graphical representation of the 3 polymorphic sites identified in the human UGT1A7 exon 1 sequence. The mutation CCC/A at codon 11 is silent. The mutations at codon 129, 131 and 208 lead to amino acid substitutions. Sequence analysis indicated the presence of 3 different polymorphisms which were assigned to UGT1A7*2, UGT1A7*3 and UGT1A7*4. The exchange at codon 11 and 208 (UGT1A7*2) and the polymorphisms at codon 129 and 131 (UGT1A7*3) did not occur singly.

FIG. 4 shows that, compared with the region around codon 11, the identified polymorphisms at position 129/131 and position 208 occur in highly conserved sequence regions. The N129K/R131K polymorphism represents the wild-type sequence of UGT1A9 in this position. W208R represents the wild-type sequence of UGT1A8 and UGT1A9 at this position.

FIG. 5 shows that the association of W208R mutations with colorectal carcinomas and inflammatory bowel diseases is highly statistically significant. Whereas mutations at codon 208 (W208R) occur in only 22% of normal controls, they are present in 73% of patients with colorectal carcinoma and in 61% of patients with inflammatory bowel diseases. A significant association with colorectal carcinoma (19% versus 7%) but not with inflammatory bowel disease was found for the UGT1A7*2 allele. The UGT1A7*4 allele was significantly associated with colorectal carcinoma and also with inflammatory bowel diseases, whereas no significant association was found for UGT1A7*3 (low significance level). The statistical significance for the presence of W208R mutations in CRC patients (73%) compared with normal controls (22%) was very high (p<0.0001). This included heterozygous (50% versus 15%, p<0.001) and homozygous (23% versus 7%, p<0.02) W208R mutations. The association was less but likewise significant for IBD patients, who showed 61% W208R mutations (p<0.0001), in 35% heterozygous and 26% homozygous individuals. An additional point to take into account concerning the 22% occurrence of W208R mutations in normal controls is that a tumor-free state at the time the blood sample was taken does not preclude later development of CRC.

The * shows significant level compared with the normal controls (Kruskal Wallis test). The meanings hereinafter are: n.s.—not significant, NC—normal controls; CRC—colorectal carcinoma and IBD—inflammatory bowel diseases.

The invention claimed is:

1. A method for identifying a person at risk of developing colorectal carcinoma on the basis of genetic predisposition, comprising the step of testing a DNA sample from said person for the presence of a CCC to CCA mutation at codon 11 of the UGT1A7 gene and a W208R mutation at codon 208 of the UGT1A7 gene, wherein the presence in said DNA sample of said mutation at codon 11 and said mutation at codon 208 indicates that said person is at risk of developing colorectal cancer.

2. The method as claimed in claim 1 wherein said testing uses genomic DNA for the DNA sample.

3. The method as claimed in claim 2, further comprising isolating genomic DNA from a blood sample by methods of column chromatography and chemical processing.

4. The method as claimed in claim 1, wherein said testing comprises carrying out PCR amplification of exon 1 of the UGT1A7 gene with subsequent sequence analysis.

5. The method as claimed in claim 4 wherein said testing comprises single strand conformation polymorphism (SSCP) analysis.

6. The method as claimed in claim 5, wherein said sequence analysis comprises sequencing by means of automated fluorescent dye sequencing.

7. The method as claimed in claim 4 wherein said PCR amplification is performed with primer sequences which bind at their 3' terminus to a polymorphic base.

8. The method as claimed in claim 7, wherein said PCR amplification is performed using probes having a wild-type UGT1A7 sequence and probes having a mutated UGT1A7 sequence.

9. The method as claimed in claim 8, wherein said PCR amplification is quantitative.

10. The method as claimed in claim 8 wherein PCR products are detected using fluorescent dyes or enzyme markers.

11. The method of claim 5, wherein said SSCP analysis comprises gel electrophoresis or temperature gradient gel electrophoresis (TGGE).

12. A method for identifying a person at risk of developing colorectal carcinoma, ulcerative colitis, and/or Crohn's disease on the basis of genetic predisposition, comprising the step of testing a DNA sample from said person for the presence of a CCC to CCA mutation at codon 11 of the UGT1A7 gene, a N129K mutation at codon 129 of the UGT1A7 gene, a R131K mutation at codon 131 of the UGT1A7 gene, and a W208R mutation at codon 208 of the UGT1A7 gene, wherein the presence in said DNA sample of said mutation at codon 11, said mutation at codon 129, said mutation at codon 131, and said mutation at codon 208 indicates that said person is at risk of developing colorectal cancer, ulcerative colitis, and/or Crohn's disease.

13. The method as claimed in claim 12 wherein said testing uses genomic DNA for the DNA sample.

14. The method as claimed in claim 13, further comprising isolating genomic DNA from a blood sample by methods of column chromatography and chemical processing.

15. The method as claimed in claim 12, wherein said testing comprises carrying out PCR amplification of exon 1 of the UGT1A7 gene with subsequent sequence analysis.

16. The method as claimed in claim 15 wherein said testing comprises single strand conformation polymorphism (SSCP) analysis.

17. The method as claimed in claim 16, wherein said sequence analysis comprises sequencing by means of automated fluorescent dye sequencing.

18. The method as claimed in claim 15 wherein said PCR amplification is performed with primer sequences which bind at their 3' terminus to a polymorphic base.

19. The method as claimed in claim 18, wherein said PCR amplification is performed using probes specific for wild-type UGT1A7 and probes specific for mutated UGT1A7.

20. The method as claimed in claim 19, wherein said PCR amplification is quantitative.

21. The method as claimed in claim 19 wherein PCR products are detected using fluorescent dyes or enzyme markers.

22. The method of claim 16, wherein said SSCP analysis comprises gel electrophoresis or temperature gradient gel electrophoresis (TGGE).

* * * * *

SEQUENCE LISTING

<160> NUMBER OF SEQ ID NOS: 57

<210> SEQ ID NO 1
<211> LENGTH: 33
<212> TYPE: DNA
<213> ORGANISM: Homo sapiens

<400> SEQUENCE: 1

-continued

| | |
|---|---|
| gcggctcgag ccacttacta tattatagga gct | 33 |

<210> SEQ ID NO 2
<211> LENGTH: 36
<212> TYPE: DNA
<213> ORGANISM: Homo sapiens

<400> SEQUENCE: 2

| | |
|---|---|
| gcggatatcc ataggcactg gctttccctg atgaca | 36 |

<210> SEQ ID NO 3
<211> LENGTH: 21
<212> TYPE: DNA
<213> ORGANISM: Homo sapiens

<400> SEQUENCE: 3

| | |
|---|---|
| gggtggactg gcctccttcc a | 21 |

<210> SEQ ID NO 4
<211> LENGTH: 21
<212> TYPE: DNA
<213> ORGANISM: Homo sapiens

<400> SEQUENCE: 4

| | |
|---|---|
| gggtggactg gcctccttcc c | 21 |

<210> SEQ ID NO 5
<211> LENGTH: 21
<212> TYPE: DNA
<213> ORGANISM: Homo sapiens

<400> SEQUENCE: 5

| | |
|---|---|
| ggcaaaaacc atgaactccc g | 21 |

<210> SEQ ID NO 6
<211> LENGTH: 30
<212> TYPE: DNA
<213> ORGANISM: Homo sapiens

<400> SEQUENCE: 6

| | |
|---|---|
| ttttttcaa attgcaggag tttgtttaag | 30 |

<210> SEQ ID NO 7
<211> LENGTH: 30
<212> TYPE: DNA
<213> ORGANISM: Homo sapiens

<400> SEQUENCE: 7

| | |
|---|---|
| ttttttcaa attgcaggag tttgtttaat | 30 |

<210> SEQ ID NO 8
<211> LENGTH: 27
<212> TYPE: DNA
<213> ORGANISM: Homo sapiens

<400> SEQUENCE: 8

| | |
|---|---|
| aaattgcagg agtttgttta aggacaa | 27 |

<210> SEQ ID NO 9
<211> LENGTH: 27
<212> TYPE: DNA
<213> ORGANISM: Homo sapiens

<400> SEQUENCE: 9

```
aaattgcagg agtttgttta atgaccg                                          27
```

<210> SEQ ID NO 10
<211> LENGTH: 27
<212> TYPE: DNA
<213> ORGANISM: Homo sapiens

<400> SEQUENCE: 10

```
ttctaagaca ttttgaaaa aataggg                                           27
```

<210> SEQ ID NO 11
<211> LENGTH: 28
<212> TYPE: DNA
<213> ORGANISM: Homo sapiens

<400> SEQUENCE: 11

```
gacgccatga ctttcaagga gagagtac                                         28
```

<210> SEQ ID NO 12
<211> LENGTH: 28
<212> TYPE: DNA
<213> ORGANISM: Homo sapiens

<400> SEQUENCE: 12

```
gacgccatga ctttcaagga gagagtat                                         28
```

<210> SEQ ID NO 13
<211> LENGTH: 27
<212> TYPE: DNA
<213> ORGANISM: Homo sapiens

<400> SEQUENCE: 13

```
tggctttccc tgatgacagt tgatacc                                          27
```

<210> SEQ ID NO 14
<211> LENGTH: 530
<212> TYPE: PRT
<213> ORGANISM: Homo sapiens

<400> SEQUENCE: 14

```
Met Ala Arg Ala Gly Trp Thr Gly Leu Leu Pro Leu Tyr Val Cys Leu
1               5                   10                  15

Leu Leu Thr Cys Gly Phe Ala Lys Ala Gly Lys Leu Leu Val Val Pro
            20                  25                  30

Met Asp Gly Ser His Trp Phe Thr Met Gln Ser Val Val Glu Lys Leu
        35                  40                  45

Ile Leu Arg Gly His Glu Val Val Val Met Pro Glu Val Ser Trp
    50                  55                  60

Gln Leu Gly Arg Ser Leu Asn Cys Thr Val Lys Thr Tyr Ser Thr Ser
65                  70                  75                  80

Tyr Thr Leu Glu Asp Gln Asp Arg Glu Phe Met Val Phe Ala Asp Ala
                85                  90                  95

Arg Trp Thr Ala Pro Leu Arg Ser Ala Phe Ser Leu Thr Ser Ser
            100                 105                 110

Ser Asn Gly Ile Phe Asp Leu Phe Phe Ser Asn Cys Arg Ser Leu Phe
        115                 120                 125

Asn Asp Arg Lys Leu Val Glu Tyr Leu Lys Glu Ser Cys Phe Asp Ala
    130                 135                 140

Val Phe Leu Asp Pro Phe Asp Ala Cys Gly Leu Ile Val Ala Lys Tyr
```

```
            145                 150                 155                 160
        Phe Ser Leu Pro Ser Val Val Phe Ala Arg Gly Ile Phe Cys His Tyr
                        165                 170                 175

Leu Glu Glu Gly Ala Gln Cys Pro Ala Pro Leu Ser Tyr Val Pro Arg
                    180                 185                 190

Leu Leu Leu Gly Phe Ser Asp Ala Met Thr Phe Lys Glu Arg Val Trp
                    195                 200                 205

Asn His Ile Met His Leu Glu Glu His Leu Phe Cys Pro Tyr Phe Phe
                    210                 215                 220

Lys Asn Val Leu Glu Ile Ala Ser Glu Ile Leu Gln Thr Pro Val Thr
        225                 230                 235                 240

Ala Tyr Asp Leu Tyr Ser His Thr Ser Ile Trp Leu Leu Arg Thr Asp
                        245                 250                 255

Phe Val Leu Glu Tyr Pro Lys Pro Val Met Pro Asn Met Ile Phe Ile
                        260                 265                 270

Gly Gly Ile Asn Cys His Gln Gly Lys Pro Val Pro Met Glu Phe Glu
                    275                 280                 285

Ala Tyr Ile Asn Ala Ser Gly Glu His Gly Ile Val Val Phe Ser Leu
                    290                 295                 300

Gly Ser Met Val Ser Glu Ile Pro Glu Lys Lys Ala Met Ala Ile Ala
        305                 310                 315                 320

Asp Ala Leu Gly Lys Ile Pro Gln Thr Val Leu Trp Arg Tyr Thr Gly
                        325                 330                 335

Thr Arg Pro Ser Asn Leu Ala Asn Asn Thr Ile Leu Val Lys Trp Leu
                    340                 345                 350

Pro Gln Asn Asp Leu Leu Gly His Pro Met Thr Arg Ala Phe Ile Thr
                    355                 360                 365

His Ala Gly Ser His Gly Val Tyr Glu Ser Ile Cys Asn Gly Val Pro
                    370                 375                 380

Met Val Met Met Pro Leu Phe Gly Asp Gln Met Asp Asn Ala Lys Arg
        385                 390                 395                 400

Met Glu Thr Lys Gly Ala Gly Val Thr Leu Asn Ala Leu Glu Met Thr
                        405                 410                 415

Ser Glu Asp Leu Glu Asn Ala Leu Lys Ala Val Ile Asn Asp Lys Ser
                    420                 425                 430

Phe Lys Glu Asn Ile Met Arg Leu Ser Ser Leu His Lys Asp Arg Pro
                    435                 440                 445

Val Glu Pro Leu Asp Leu Ala Val Phe Trp Val Glu Phe Val Met Arg
                    450                 455                 460

His Lys Gly Ala Pro His Leu Arg Pro Ala Ala His Asp Leu Thr Trp
        465                 470                 475                 480

Tyr Gln Tyr His Ser Leu Asp Val Ile Gly Phe Leu Leu Ala Val Val
                        485                 490                 495

Leu Thr Val Ala Phe Ile Thr Phe Lys Cys Cys Ala Tyr Gly Tyr Arg
                        500                 505                 510

Lys Cys Leu Gly Lys Lys Gly Arg Val Lys Lys Ala His Lys Ser Lys
                    515                 520                 525

Thr His
            530

<210> SEQ ID NO 15
<211> LENGTH: 530
<212> TYPE: PRT
<213> ORGANISM: Homo sapiens
```

<400> SEQUENCE: 15

```
Met Ala Arg Ala Gly Trp Thr Gly Leu Leu Pro Leu Tyr Val Cys Leu
1               5                   10                  15

Leu Leu Thr Cys Gly Phe Ala Lys Ala Gly Lys Leu Leu Val Val Pro
            20                  25                  30

Met Asp Gly Ser His Trp Phe Thr Met Gln Ser Val Val Glu Lys Leu
        35                  40                  45

Ile Leu Arg Gly His Glu Val Val Val Met Pro Glu Val Ser Trp
50                  55                  60

Gln Leu Gly Arg Ser Leu Asn Cys Thr Val Lys Thr Tyr Ser Thr Ser
65                  70                  75                  80

Tyr Thr Leu Glu Asp Gln Asp Arg Glu Phe Met Val Phe Ala Asp Ala
                85                  90                  95

Arg Trp Thr Ala Pro Leu Arg Ser Ala Phe Ser Leu Leu Thr Ser Ser
                100                 105                 110

Ser Asn Gly Ile Phe Asp Leu Phe Phe Ser Asn Cys Arg Ser Leu Phe
            115                 120                 125

Asn Asp Arg Lys Leu Val Glu Tyr Leu Lys Glu Ser Cys Phe Asp Ala
130                 135                 140

Val Phe Leu Asp Pro Phe Asp Ala Cys Gly Leu Ile Val Ala Lys Tyr
145                 150                 155                 160

Phe Ser Leu Pro Ser Val Val Phe Ala Arg Gly Ile Phe Cys His Tyr
                165                 170                 175

Leu Glu Glu Gly Ala Gln Cys Pro Ala Pro Leu Ser Tyr Val Pro Arg
                180                 185                 190

Leu Leu Leu Gly Phe Ser Asp Ala Met Thr Phe Lys Glu Arg Val Arg
            195                 200                 205

Asn His Ile Met His Leu Glu Glu His Leu Phe Cys Pro Tyr Phe Phe
210                 215                 220

Lys Asn Val Leu Glu Ile Ala Ser Glu Ile Leu Gln Thr Pro Val Thr
225                 230                 235                 240

Ala Tyr Asp Leu Tyr Ser His Thr Ser Ile Trp Leu Leu Arg Thr Asp
                245                 250                 255

Phe Val Leu Glu Tyr Pro Lys Pro Val Met Pro Asn Met Ile Phe Ile
                260                 265                 270

Gly Gly Ile Asn Cys His Gln Gly Lys Pro Val Pro Met Glu Phe Glu
            275                 280                 285

Ala Tyr Ile Asn Ala Ser Gly Glu His Gly Ile Val Val Phe Ser Leu
290                 295                 300

Gly Ser Met Val Ser Glu Ile Pro Glu Lys Lys Ala Met Ala Ile Ala
305                 310                 315                 320

Asp Ala Leu Gly Lys Ile Pro Gln Thr Val Leu Trp Arg Tyr Thr Gly
                325                 330                 335

Thr Arg Pro Ser Asn Leu Ala Asn Asn Thr Ile Leu Val Lys Trp Leu
                340                 345                 350

Pro Gln Asn Asp Leu Leu Gly His Pro Met Thr Arg Ala Phe Ile Thr
            355                 360                 365

His Ala Gly Ser His Gly Val Tyr Glu Ser Ile Cys Asn Gly Val Pro
370                 375                 380

Met Val Met Met Pro Leu Phe Gly Asp Gln Met Asp Asn Ala Lys Arg
385                 390                 395                 400

Met Glu Thr Lys Gly Ala Gly Val Thr Leu Asn Ala Leu Glu Met Thr
```

```
                        405                 410                 415
Ser Glu Asp Leu Glu Asn Ala Leu Lys Ala Val Ile Asn Asp Lys Ser
                420                 425                 430

Phe Lys Glu Asn Ile Met Arg Leu Ser Ser Leu His Lys Asp Arg Pro
            435                 440                 445

Val Glu Pro Leu Asp Leu Ala Val Phe Trp Val Glu Phe Val Met Arg
        450                 455                 460

His Lys Gly Ala Pro His Leu Arg Pro Ala Ala His Asp Leu Thr Trp
465                 470                 475                 480

Tyr Gln Tyr His Ser Leu Asp Val Ile Gly Phe Leu Leu Ala Val Val
                485                 490                 495

Leu Thr Val Ala Phe Ile Thr Phe Lys Cys Cys Ala Tyr Gly Tyr Arg
            500                 505                 510

Lys Cys Leu Gly Lys Lys Gly Arg Val Lys Lys Ala His Lys Ser Lys
        515                 520                 525

Thr His
    530

<210> SEQ ID NO 16
<211> LENGTH: 530
<212> TYPE: PRT
<213> ORGANISM: Homo sapiens

<400> SEQUENCE: 16

Met Ala Arg Ala Gly Trp Thr Gly Leu Leu Pro Leu Tyr Val Cys Leu
1               5                   10                  15

Leu Leu Thr Cys Gly Phe Ala Lys Ala Gly Lys Leu Leu Val Val Pro
            20                  25                  30

Met Asp Gly Ser His Trp Phe Thr Met Gln Ser Val Val Glu Lys Leu
        35                  40                  45

Ile Leu Arg Gly His Glu Val Val Val Met Pro Glu Val Ser Trp
    50                  55                  60

Gln Leu Gly Arg Ser Leu Asn Cys Thr Val Lys Thr Tyr Ser Thr Ser
65                  70                  75                  80

Tyr Thr Leu Glu Asp Gln Asp Arg Glu Phe Met Val Phe Ala Asp Ala
                85                  90                  95

Arg Trp Thr Ala Pro Leu Arg Ser Ala Phe Ser Leu Leu Thr Ser Ser
            100                 105                 110

Ser Asn Gly Ile Phe Asp Leu Phe Phe Ser Asn Cys Arg Ser Leu Phe
        115                 120                 125

Lys Asp Lys Lys Leu Val Glu Tyr Leu Lys Glu Ser Cys Phe Asp Ala
    130                 135                 140

Val Phe Leu Asp Pro Phe Asp Ala Cys Gly Leu Ile Val Ala Lys Tyr
145                 150                 155                 160

Phe Ser Leu Pro Ser Val Val Phe Ala Arg Gly Ile Phe Cys His Tyr
                165                 170                 175

Leu Glu Glu Gly Ala Gln Cys Pro Ala Pro Leu Ser Tyr Val Pro Arg
            180                 185                 190

Leu Leu Leu Gly Phe Ser Asp Ala Met Thr Phe Lys Glu Arg Val Trp
        195                 200                 205

Asn His Ile Met His Leu Glu Glu His Leu Phe Cys Pro Tyr Phe Phe
    210                 215                 220

Lys Asn Val Leu Glu Ile Ala Ser Glu Ile Leu Gln Thr Pro Val Thr
225                 230                 235                 240
```

```
Ala Tyr Asp Leu Tyr Ser His Thr Ser Ile Trp Leu Arg Thr Asp
            245                 250                 255

Phe Val Leu Glu Tyr Pro Lys Pro Val Met Pro Asn Met Ile Phe Ile
            260                 265                 270

Gly Gly Ile Asn Cys His Gln Gly Lys Pro Val Pro Met Glu Phe Glu
            275                 280                 285

Ala Tyr Ile Asn Ala Ser Gly Glu His Gly Ile Val Val Phe Ser Leu
            290                 295                 300

Gly Ser Met Val Ser Glu Ile Pro Glu Lys Lys Ala Met Ala Ile Ala
305                 310                 315                 320

Asp Ala Leu Gly Lys Ile Pro Gln Thr Val Leu Trp Arg Tyr Thr Gly
            325                 330                 335

Thr Arg Pro Ser Asn Leu Ala Asn Asn Thr Ile Leu Val Lys Trp Leu
            340                 345                 350

Pro Gln Asn Asp Leu Leu Gly His Pro Met Thr Arg Ala Phe Ile Thr
            355                 360                 365

His Ala Gly Ser His Gly Val Tyr Glu Ser Ile Cys Asn Gly Val Pro
            370                 375                 380

Met Val Met Met Pro Leu Phe Gly Asp Gln Met Asp Asn Ala Lys Arg
385                 390                 395                 400

Met Glu Thr Lys Gly Ala Gly Val Thr Leu Asn Ala Leu Glu Met Thr
            405                 410                 415

Ser Glu Asp Leu Glu Asn Ala Leu Lys Ala Val Ile Asn Asp Lys Ser
            420                 425                 430

Phe Lys Glu Asn Ile Met Arg Leu Ser Ser Leu His Lys Asp Arg Pro
            435                 440                 445

Val Glu Pro Leu Asp Leu Ala Val Phe Trp Val Glu Phe Val Met Arg
            450                 455                 460

His Lys Gly Ala Pro His Leu Arg Pro Ala Ala His Asp Leu Thr Trp
465                 470                 475                 480

Tyr Gln Tyr His Ser Leu Asp Val Ile Gly Phe Leu Leu Ala Val Val
            485                 490                 495

Leu Thr Val Ala Phe Ile Thr Phe Lys Cys Cys Ala Tyr Gly Tyr Arg
            500                 505                 510

Lys Cys Leu Gly Lys Lys Gly Arg Val Lys Lys Ala His Lys Ser Lys
            515                 520                 525

Thr His
    530

<210> SEQ ID NO 17
<211> LENGTH: 530
<212> TYPE: PRT
<213> ORGANISM: Homo sapiens

<400> SEQUENCE: 17

Met Ala Arg Ala Gly Trp Thr Gly Leu Leu Pro Leu Tyr Val Cys Leu
1               5                   10                  15

Leu Leu Thr Cys Gly Phe Ala Lys Ala Gly Lys Leu Leu Val Val Pro
            20                  25                  30

Met Asp Gly Ser His Trp Phe Thr Met Gln Ser Val Val Glu Lys Leu
            35                  40                  45

Ile Leu Arg Gly His Glu Val Val Val Met Pro Glu Val Ser Trp
            50                  55                  60

Gln Leu Gly Arg Ser Leu Asn Cys Thr Val Lys Thr Tyr Ser Thr Ser
65                  70                  75                  80
```

-continued

```
Tyr Thr Leu Glu Asp Gln Asp Arg Glu Phe Met Val Phe Ala Asp Ala
                 85                  90                  95

Arg Trp Thr Ala Pro Leu Arg Ser Ala Phe Ser Leu Leu Thr Ser Ser
            100                 105                 110

Ser Asn Gly Ile Phe Asp Leu Phe Phe Ser Asn Cys Arg Ser Leu Phe
        115                 120                 125

Lys Asp Lys Lys Leu Val Glu Tyr Leu Lys Glu Ser Cys Phe Asp Ala
    130                 135                 140

Val Phe Leu Asp Pro Phe Asp Ala Cys Gly Leu Ile Val Ala Lys Tyr
145                 150                 155                 160

Phe Ser Leu Pro Ser Val Val Phe Ala Arg Gly Ile Phe Cys His Tyr
                165                 170                 175

Leu Glu Glu Gly Ala Gln Cys Pro Ala Pro Leu Ser Tyr Val Pro Arg
            180                 185                 190

Leu Leu Leu Gly Phe Ser Asp Ala Met Thr Phe Lys Glu Arg Val Arg
        195                 200                 205

Asn His Ile Met His Leu Glu Glu His Leu Phe Cys Pro Tyr Phe Phe
    210                 215                 220

Lys Asn Val Leu Glu Ile Ala Ser Glu Ile Leu Gln Thr Pro Val Thr
225                 230                 235                 240

Ala Tyr Asp Leu Tyr Ser His Thr Ser Ile Trp Leu Leu Arg Thr Asp
                245                 250                 255

Phe Val Leu Glu Tyr Pro Lys Pro Val Met Pro Asn Met Ile Phe Ile
            260                 265                 270

Gly Gly Ile Asn Cys His Gln Gly Lys Pro Val Pro Met Glu Phe Glu
        275                 280                 285

Ala Tyr Ile Asn Ala Ser Gly Glu His Gly Ile Val Val Phe Ser Leu
    290                 295                 300

Gly Ser Met Val Ser Glu Ile Pro Glu Lys Lys Ala Met Ala Ile Ala
305                 310                 315                 320

Asp Ala Leu Gly Lys Ile Pro Gln Thr Val Leu Trp Arg Tyr Thr Gly
                325                 330                 335

Thr Arg Pro Ser Asn Leu Ala Asn Asn Thr Ile Leu Val Lys Trp Leu
            340                 345                 350

Pro Gln Asn Asp Leu Leu Gly His Pro Met Thr Arg Ala Phe Ile Thr
        355                 360                 365

His Ala Gly Ser His Gly Val Tyr Glu Ser Ile Cys Asn Gly Val Pro
    370                 375                 380

Met Val Met Met Pro Leu Phe Gly Asp Gln Met Asp Asn Ala Lys Arg
385                 390                 395                 400

Met Glu Thr Lys Gly Ala Gly Val Thr Leu Asn Ala Leu Glu Met Thr
                405                 410                 415

Ser Glu Asp Leu Glu Asn Ala Leu Lys Ala Val Ile Asn Asp Lys Ser
            420                 425                 430

Phe Lys Glu Asn Ile Met Arg Leu Ser Ser Leu His Lys Asp Arg Pro
        435                 440                 445

Val Glu Pro Leu Asp Leu Ala Val Phe Trp Val Glu Phe Val Met Arg
    450                 455                 460

His Lys Gly Ala Pro His Leu Arg Pro Ala His Asp Leu Thr Trp
465                 470                 475                 480

Tyr Gln Tyr His Ser Leu Asp Val Ile Gly Phe Leu Leu Ala Val Val
                485                 490                 495
```

Leu Thr Val Ala Phe Ile Thr Phe Lys Cys Cys Ala Tyr Gly Tyr Arg
            500                 505                 510

Lys Cys Leu Gly Lys Lys Gly Arg Val Lys Lys Ala His Lys Ser Lys
        515                 520                 525

Thr His
    530

<210> SEQ ID NO 18
<211> LENGTH: 1593
<212> TYPE: DNA
<213> ORGANISM: Homo sapiens

<400> SEQUENCE: 18

| | | | | | | |
|---|---|---|---|---|---|---|
| atggctcgtg | cagggtggac | tggcctcctt | ccctatatg | tgtgtctact | gctgacctgt | 60 |
| ggctttgcca | aggcagggaa | gctgctggta | gtgcccatgg | atgggagcca | ctggttcacc | 120 |
| atgcagtcgg | tggtggagaa | actcatcctc | aggggggcatg | aggtggtcgt | agtcatgcca | 180 |
| gaggtgagtt | ggcaactggg | aagatcactg | aattgcacag | tgaagactta | ctcaacctca | 240 |
| tacactctgg | aggatcagga | ccgggagttc | atggttttttg | ccgatgctcg | ctggacggca | 300 |
| ccattgcgaa | gtgcattttc | tctattaaca | agttcatcca | atggtatttt | tgacttattt | 360 |
| ttttcaaatt | gcaggagttt | gtttaatgac | cgaaaattag | tagaatactt | aaaggagagt | 420 |
| tgttttgatg | cagtgtttct | cgatcctttt | gatgcctgtg | gcttaattgt | tgccaaatat | 480 |
| ttctccctcc | cctctgtggt | cttcgccagg | ggaatatttt | gccactatct | tgaagaaggt | 540 |
| gcacagtgcc | ctgctcctct | ttcctatgtc | cccagacttc | tcttagggtt | ctcagacgcc | 600 |
| atgactttca | aggagagagt | atggaaccac | atcatgcact | ggaggaaca | tttattttgc | 660 |
| ccctattttt | tcaaaaatgt | cttagaaata | gcctctgaaa | ttctccaaac | ccctgtcacg | 720 |
| gcatatgatc | tctacagcca | cacatcaatt | tggttgttgc | gaactgactt | tgttttggag | 780 |
| tatcccaaac | ccgtgatgcc | caatgatc | ttcattggtg | gtatcaactg | tcatcaggga | 840 |
| aagccagtgc | ctatggaatt | tgaagcctac | attaatgctt | ctggagaaca | tggaattgtg | 900 |
| gttttctctt | tgggatcaat | ggtctcagaa | attccagaga | agaaagctat | ggcaattgct | 960 |
| gatgctttgg | gcaaaatccc | tcagacagtc | ctgtggcggt | acactggaac | ccgaccatcg | 1020 |
| aatcttgcga | caacacgat | acttgttaag | tggctacccc | aaaacgatct | gcttggtcac | 1080 |
| ccgatgaccc | gtgcctttat | cacccatgct | ggttcccatg | gtgtttatga | agcatatgc | 1140 |
| aatgccgttc | ccatggtgat | gatgcccttg | tttggtgatc | agatggacaa | tgcaaagcgc | 1200 |
| atggagacta | agggagctgg | agtgaccctg | aatgctctgg | aaatgacttc | tgaagattta | 1260 |
| gaaaatgctc | taaaagcagt | catcaatgac | aaaagtttca | aggagaacat | catgcgcctc | 1320 |
| tccagccttc | acaaggaccg | cccggtggag | ccgctggacc | tggccgtgtt | ctgggtggag | 1380 |
| tttgtgatga | ggcacaaggg | cgcgccacac | ctgcgcccg | cagcccacga | cctcacctgg | 1440 |
| taccagtacc | attccttgga | cgtgattggt | ttcctcttgg | ccgtcgtgct | gacagtggcc | 1500 |
| ttcatcacct | ttaaatgttg | tgcttatggc | taccggaaat | gcttggggaa | aaagggcga | 1560 |
| gttaagaaag | cccacaaatc | caagacccat | tga | | | 1593 |

<210> SEQ ID NO 19
<211> LENGTH: 1593
<212> TYPE: DNA
<213> ORGANISM: Homo sapiens

<400> SEQUENCE: 19

```
atggctcgtg cagggtggac tggcctcctt ccactatatg tgtgtctact gctgacctgt    60
ggctttgcca aggcagggaa gctgctggta gtgcccatgg atgggagcca ctggttcacc   120
atgcagtcgg tggtggagaa actcatcctc agggggcatg aggtggtcgt agtcatgcca   180
gaggtgagtt ggcaactggg aagatcactg aattgcacag tgaagactta ctcaacctca   240
tacactctgg aggatcagga ccgggagttc atggttttg ccgatgctcg ctggacggca    300
ccattgcgaa gtgcattttc tctattaaca agttcatcca atggtatttt tgacttattt   360
ttttcaaatt gcaggagttt gtttaatgac cgaaaattag tagaatactt aaaggagagt   420
tgttttgatg cagtgtttct cgatcctttt gatgcctgtg gcttaattgt tgccaaatat   480
ttctccctcc cctctgtggt cttcgccagg ggaatatttt gccactatct gaagaaggt    540
gcacagtgcc ctgctcctct ttcctatgtc cccagacttc tcttagggtt ctcagacgcc   600
atgactttca aggagagagt acggaaccac atcatgcact ggaggaaca  tttattttgc    660
ccctattttt tcaaaaatgt cttagaaata gcctctgaaa ttctccaaac ccctgtcacg   720
gcatatgatc tctacagcca cacatcaatt tggttgttgc gaactgactt tgttttggag   780
tatcccaaac ccgtgatgcc caatatgatc ttcattggtg gtatcaactg tcatcaggga   840
aagccagtgc ctatggaatt tgaagcctac attaatgctt ctggagaaca tggaattgtg   900
gttttctctt gggatcaat  ggtctcagaa attccagaga gaaagctat   ggcaattgct    960
gatgctttgg gcaaaatccc tcagacagtc ctgtggcggt acactggaac ccgaccatcg  1020
aatcttgcga caacacgat  acttgttaag tggctacccc aaaacgatct gcttggtcac  1080
ccgatgaccc gtgcctttat cacccatgct ggttcccatg gtgtttatga agcatatgc   1140
aatggcgttc catggtgat  gatgcccttg tttggtgatc agatggacaa tgcaaagcgc  1200
atggagacta agggagctgg agtgaccctg aatgctctgg aaatgacttc tgaagattta  1260
gaaaatgctc taaaagcagt catcaatgac aaaagtttca aggagaacat catgcgcctc  1320
tccagccttc acaaggaccg cccggtggag ccgctggacc tggccgtgtt ctgggtggag  1380
tttgtgatga ggcacaaggg cgcgccacac ctgcgcccg  cagcccacga cctcacctgg  1440
taccagtacc attccttgga cgtgattggt ttcctcttgg ccgtcgtgct gacagtggcc  1500
ttcatcacct ttaaatgttg tgcttatggc taccggaaat gcttggggaa aaaagggcga  1560
gttaagaaag cccacaaatc caagacccat tga                               1593
```

<210> SEQ ID NO 20
<211> LENGTH: 1593
<212> TYPE: DNA
<213> ORGANISM: Homo sapiens

<400> SEQUENCE: 20

```
atggctcgtg cagggtggac tggcctcctt ccctatatg  tgtgtctact gctgacctgt    60
ggctttgcca aggcagggaa gctgctggta gtgcccatgg atgggagcca ctggttcacc   120
atgcagtcgg tggtggagaa actcatcctc agggggcatg aggtggtcgt agtcatgcca   180
gaggtgagtt ggcaactggg aagatcactg aattgcacag tgaagactta ctcaacctca   240
tacactctgg aggatcagga ccgggagttc atggttttg  ccgatgctcg ctggacggca    300
ccattgcgaa gtgcattttc tctattaaca agttcatcca atggtatttt tgacttattt   360
ttttcaaatt gcaggagttt gtttaaggac aaaaaattag tagaatactt aaaggagagt   420
tgttttgatg cagtgtttct cgatcctttt gatgcctgtg gcttaattgt tgccaaatat   480
ttctccctcc cctctgtggt cttcgccagg ggaatatttt gccactatct gaagaaggt    540
```

```
gcacagtgcc ctgctcctct ttcctatgtc cccagacttc tcttagggtt ctcagacgcc      600
atgactttca aggagagagt atggaaccac atcatgcact tggaggaaca tttattttgc      660
ccctattttt tcaaaaatgt cttagaaata gcctctgaaa ttctccaaac ccctgtcacg      720
gcatatgatc tctacagcca cacatcaatt tggttgttgc gaactgactt tgttttggag      780
tatcccaaac ccgtgatgcc caatatgatc ttcattggtg gtatcaactg tcatcaggga      840
aagccagtgc ctatggaatt tgaagcctac attaatgctt ctggagaaca tggaattgtg      900
gttttctctt tgggatcaat ggtctcagaa attccagaga agaaagctat ggcaattgct      960
gatgctttgg gcaaaatccc tcagacagtc ctgtggcggt acactggaac ccgaccatcg     1020
aatcttgcga acaacacgat acttgttaag tggctacccc aaaacgatct gcttggtcac     1080
ccgatgaccc gtgcctttat cacccatgct ggttcccatg gtgtttatga agcatatgc      1140 aatggcgttc ccatggtgat gatgcccttg tttggtgatc agatggacaa tgcaaagcgc     1200
atggagacta agggagctgg agtgaccctg aatgctctgg aaatgacttc tgaagattta     1260
gaaaatgctc taaaagcagt catcaatgac aaaagtttca aggagaacat catgcgcctc     1320
tccagccttc acaaggaccg cccggtggag ccgctggacc tggccgtgtt ctgggtggag     1380
tttgtgatga ggcacaaggg cgcgccacac ctgcgcccg  cagcccacga cctcacctgg     1440
taccagtacc attccttgga cgtgattggt ttcctcttgg ccgtcgtgct gacagtggcc     1500
ttcatcacct ttaaatgttg tgcttatggc taccggaaat gcttggggaa aaagggcga      1560 gttaagaaag cccacaaatc caagacccat tga                                  1593

<210> SEQ ID NO 21
<211> LENGTH: 1593
<212> TYPE: DNA
<213> ORGANISM: Homo sapiens

<400> SEQUENCE: 21
atggctcgtg cagggtggac tggcctcctt ccactatatg tgtgtctact gctgacctgt       60
ggctttgcca aggcagggaa gctgctggta gtgcccatgg atgggagcca ctggttcacc      120
atgcagtcgg tggtggagaa actcatcctc agggggcatg aggtggtcgt agtcatgcca      180
gaggtgagtt ggcaactggg aagatcactg aattgcacag tgaagactta ctcaacctca      240
tacactctgg aggatcagga ccgggagttc atggtttttg ccgatgctcg ctggacggca      300
ccattgcgaa gtcattttc tctattaaca agttcatcca atggtatttt tgacttattt      360
ttttcaaatt gcaggagttt gtttaaggac aaaaaattag tagaatactt aaaggagagt      420
tgttttgatg cagtgtttct cgatcctttt gatgcctgtg gcttaattgt tgccaaatat      480
ttctccctcc cctctgtggt cttcgccagg gaatattttt gccactatct tgaagaaggt      540
gcacagtgcc ctgctcctct ttcctatgtc cccagacttc tcttagggtt ctcagacgcc      600
atgactttca aggagagagt acggaaccac atcatgcact tggaggaaca tttattttgc      660
ccctattttt tcaaaaatgt cttagaaata gcctctgaaa ttctccaaac ccctgtcacg      720
gcatatgatc tctacagcca cacatcaatt tggttgttgc gaactgactt tgttttggag      780
tatcccaaac ccgtgatgcc caatatgatc ttcattggtg gtatcaactg tcatcaggga      840
aagccagtgc ctatggaatt tgaagcctac attaatgctt ctggagaaca tggaattgtg      900
gttttctctt tgggatcaat ggtctcagaa attccagaga agaaagctat ggcaattgct      960
gatgctttgg gcaaaatccc tcagacagtc ctgtggcggt acactggaac ccgaccatcg     1020
```

```
aatcttgcga acaacacgat acttgttaag tggctacccc aaaacgatct gcttggtcac      1080
ccgatgaccc gtgcctttat cacccatgct ggttcccatg gtgtttatga aagcatatgc      1140
aatggcgttc ccatggtgat gatgcccttg tttggtgatc agatggacaa tgcaaagcgc      1200
atggagacta agggagctgg agtgaccctg aatgctctgg aaatgacttc tgaagattta      1260
gaaaatgctc taaaagcagt catcaatgac aaaagtttca aggagaacat catgcgcctc      1320
tccagccttc acaaggaccg cccggtggag ccgctggacc tggccgtgtt ctgggtggag      1380
tttgtgatga ggcacaaggg cgcgccacac ctgcgccccg cagcccacga cctcacctgg      1440
taccagtacc attccttgga cgtgattggt ttcctcttgg ccgtcgtgct gacagtggcc      1500
ttcatcacct ttaaatgttg tgcttatggc taccggaaat gcttggggaa aaaagggcga      1560
gttaagaaag cccacaaatc caagacccat tga                                  1593
```

<210> SEQ ID NO 22
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: DNA encoding residues 128-132 of UGT1A7*1 as
      shown in Figure 3

<400> SEQUENCE: 22
tttaatgacc gaaaa                                                        15

<210> SEQ ID NO 23
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: amino acid residues 128-132 of UGT1A7*1 as
      shown in Figure 3

<400> SEQUENCE: 23

Phe Asn Asp Arg Lys
1               5

<210> SEQ ID NO 24
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: DNA encoding residues 128-132 of UGT1A7*2 as
      shown in Figure 3

<400> SEQUENCE: 24
tttaatgacc gaaaa                                                        15

<210> SEQ ID NO 25
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: amino acid residues 128-132 of UGT1A7*2 as
      shown in Figure 3

<400> SEQUENCE: 25

```
Phe Asn Asp Arg Lys
1               5

<210> SEQ ID NO 26
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: DNA encoding residues 128-132 of UGT1A7*3 as
      shown in Figure 3

<400> SEQUENCE: 26
tttaaggaca aaaaa                                                15

<210> SEQ ID NO 27
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: amino acid residues 128-132 of UGT1A7*3 as
      shown in Figure 3

<400> SEQUENCE: 27

Phe Lys Asp Lys Lys
1               5

<210> SEQ ID NO 28
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: DNA encoding residues 128-132 of UGT1A7*4 as
      shown in Figure 3

<400> SEQUENCE: 28
tttaaggaca aaaaa                                                15

<210> SEQ ID NO 29
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: amino acid residues 128-132 of UGT1A7*4 as
      shown in Figure 3

<400> SEQUENCE: 29

Phe Lys Asp Lys Lys
1               5

<210> SEQ ID NO 30
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: amino acid residues 7-10 of UGT1A1 as
      shown in Figure 4

<400> SEQUENCE: 30

Gly Gly Arg Pro
```

```
<210> SEQ ID NO 31
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: amino acid residues 12-15 of UGT1A3 as
                        shown in Figure 4

<400> SEQUENCE: 31

Leu Val Leu Gly
1

<210> SEQ ID NO 32
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: amino acid residues 127-134 of UGT1A1 as
                        shown in Figure 4

<400> SEQUENCE: 32

Leu Leu His Asn Lys Glu Leu Met
1               5

<210> SEQ ID NO 33
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: amino acid residues 205-1213of UGT1A1 as
                        shown in Figure 4

<400> SEQUENCE: 33

Gln Arg Val Lys Asn Met Leu Ile Ala
1               5

<210> SEQ ID NO 34
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: amino acid residues 7-15 of UGT1A3 as
                        shown in Figure 4

<400> SEQUENCE: 34

Val Pro Leu Pro Trp Leu Ala Thr Gly
1               5

<210> SEQ ID NO 35
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: amino acid residues 127-134 of UGT1A3 as
                        shown in Figure 4

<400> SEQUENCE: 35
```

```
-continued

Leu Leu His Asn Glu Ala Leu Ile
1               5

<210> SEQ ID NO 36
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: amino acid residues 205-1213f UGT1A3 as
                        shown in Figure 4

<400> SEQUENCE: 36

Gln Arg Val Lys Asn Met Leu Tyr Pro
1               5

<210> SEQ ID NO 37
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: amino acid residues 7-15 of UGT1A4 as
                        shown in Figure 4

<400> SEQUENCE: 37

Val Pro Leu Pro Gln Leu Ala Thr Gly
1               5

<210> SEQ ID NO 38
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: amino acid residues 127-134 of UGT1A4 as
                        shown in Figure 4

<400> SEQUENCE: 38

Leu Leu His Asn Glu Ala Leu Ile
1               5

<210> SEQ ID NO 39
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: amino acid residues 205-213 of UGT1A4 as
                        shown in Figure 4

<400> SEQUENCE: 39

Gln Arg Val Lys Asn Met Leu Tyr Pro
1               5

<210> SEQ ID NO 40
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: amino acid residues 7-15 of UGT1A5 as
                        shown in Figure 4

<400> SEQUENCE: 40
```

```
Val Pro Leu Pro Arg Leu Ala Thr Gly
1               5

<210> SEQ ID NO 41
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: amino acid residues 127-134 of UGT1A5 as
                        shown in Figure 4

<400> SEQUENCE: 41

Leu Leu His Asn Glu Ala Leu Ile
1               5

<210> SEQ ID NO 42
<211> LENGTH: 8
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: amino acid residues 205-213 of UGT1A5 as
                        shown in Figure 4

<400> SEQUENCE: 42

Leu Leu His Asn Glu Ala Leu Ile
1               5

<210> SEQ ID NO 43
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: amino acid residues 7-15 of UGT1A6 as
                        shown in Figure 4

<400> SEQUENCE: 43

Arg Ser Phe Gln Arg Ile Ser Ala Gly
1               5

<210> SEQ ID NO 44
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: amino acid residues 127-134 of UGT1A6 as
                        shown in Figure 4

<400> SEQUENCE: 44

Leu Leu Gln Asp Arg Asp Thr Leu
1               5

<210> SEQ ID NO 45
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: amino acid residues 205-213 of UGT1A6 as
                        shown in Figure 4
```

-continued

```
<400> SEQUENCE: 45

Gln Arg Val Ala Asn Phe Leu Val Asn
1               5

<210> SEQ ID NO 46
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: amino acid residues 7-15 of UGT1A7 as
                        shown in Figure 4

<400> SEQUENCE: 46

Thr Gly Leu Leu Pro Leu Tyr Val Cys
1               5

<210> SEQ ID NO 47
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: amino acid residues 127-134 of UGT1A7 as
                        shown in Figure 4

<400> SEQUENCE: 47

Leu Phe Asn Asp Arg Lys Leu Val
1               5

<210> SEQ ID NO 48
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: amino acid residues 205-213 of UGT1A7 as
                        shown in Figure 4

<400> SEQUENCE: 48

Glu Arg Val Trp Asn His Ile Met His
1               5

<210> SEQ ID NO 49
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: amino acid residues 7-15 of UGT1A8 as
                        shown in Figure 4

<400> SEQUENCE: 49

Thr Ser Pro Ile Pro Leu Cys Val Ser
1               5

<210> SEQ ID NO 50
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: amino acid residues 127-134 of UGT1A8 as
                        shown in Figure 4
```

```
<400> SEQUENCE: 50

Leu Phe Asn Asp Arg Lys Leu Val
1               5

<210> SEQ ID NO 51
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: amino acid residues 205-213 of UGT1A8 as
                        shown in Figure 4

<400> SEQUENCE: 51

Glu Arg Val Arg Asn His Ile Met His
1               5

<210> SEQ ID NO 52
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: amino acid residues 7-15 of UGT1A9 as
                        shown in Figure 4

<400> SEQUENCE: 52

Thr Ser Pro Leu Pro Leu Cys Val Cys
1               5

<210> SEQ ID NO 53
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: amino acid residues 127-134 of UGT1A9 as
                        shown in Figure 4

<400> SEQUENCE: 53

Leu Phe Lys Asp Lys Lys Leu Val
1               5

<210> SEQ ID NO 54
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: amino acid residues 205-213 of UGT1A9 as
                        shown in Figure 4

<400> SEQUENCE: 54

Glu Arg Val Arg Asn His Ile Met His
1               5

<210> SEQ ID NO 55
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: amino acid residues 7-15 of UGT1A10 as
```

-continued shown in Figure 4

<400> SEQUENCE: 55

Asp Gln Pro Arg Ser Phe Met Cys Val
1               5

<210> SEQ ID NO 56
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: amino acid residues 127-134 of UGT1A10 as
      shown in Figure 4

<400> SEQUENCE: 56

Leu Phe Asn Asp Arg Lys Leu Val
1               5

<210> SEQ ID NO 57
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: amino acid residues 205-213 of UGT1A10 as
      shown in Figure 4

<400> SEQUENCE: 57

Glu Arg Val Trp Asn His Ile Val His
1               5